(12) United States Patent
Lima (10) Patent No.: US 11,771,546 B2
(45) Date of Patent: Oct. 3, 2023

(54) HYDRAULIC MUSCLE FROM HOLLOW WRAPPED CARBON NANOTUBE YARN

(71) Applicant: Lintec of America, Inc., Richardson, TX (US)

(72) Inventor: Marcio Dias Lima, Richardson, TX (US)

(73) Assignee: LINTEC OF AMERICA, INC., Plano, TX (US)

( * ) Notice: Subject to any disclaimer, the term of this patent is extended or adjusted under 35 U.S.C. 154(b) by 604 days.

(21) Appl. No.: 16/970,572

(22) PCT Filed: Feb. 22, 2019

(86) PCT No.: PCT/US2019/019233
§ 371 (c)(1),
(2) Date: Aug. 17, 2020

(87) PCT Pub. No.: WO2019/165265
PCT Pub. Date: Aug. 29, 2019

(65) Prior Publication Data
US 2021/0000587 A1    Jan. 7, 2021

Related U.S. Application Data

(60) Provisional application No. 62/634,122, filed on Feb. 22, 2018.

(51) Int. Cl.
*A61F 2/08* (2006.01)
*C01B 32/162* (2017.01)
(Continued)

(52) U.S. Cl.
CPC ............... *A61F 2/08* (2013.01); *B01J 23/50* (2013.01); *C01B 32/162* (2017.08); *D02G 3/448* (2013.01);
(Continued)

(58) Field of Classification Search
CPC ............... A61F 2/08; A61F 2002/0894; A61F 2210/0057; A61F 2210/0066; B01J 23/50;
(Continued)

(56) References Cited

U.S. PATENT DOCUMENTS

| | | | |
|---|---|---|---|
| 2015/0152852 A1* | 6/2015 | Li | D01H 1/10 60/527 |
| 2015/0369264 A1* | 12/2015 | Felt | G01D 5/14 92/90 |

(Continued)

FOREIGN PATENT DOCUMENTS

| | | |
|---|---|---|
| JP | 2015-533521 | 11/2015 |
| KR | 20170021528 A | 2/2017 |

(Continued)

OTHER PUBLICATIONS

International Search Report issued in corresponding International Application No. PCT/US2019/019233, dated Apr. 23, 2019 (4 pages).

(Continued)

*Primary Examiner* — Keri J Nelson
*Assistant Examiner* — Rebecca Lynee Zimmerman
(74) *Attorney, Agent, or Firm* — GREENBLUM & BERNSTEIN, P.L.C.

(57) ABSTRACT

A hydraulic muscle comprises a hollow carbon nanotube (CNT) yarn tube comprising: a plurality of CNT sheets twisted and wrapped in form of a hollow tube; and a binding agent infiltrated in the plurality of CNT sheets that binds the plurality of the CNT sheets together. A method of manufacturing a hydraulic muscle comprises: twisting and wrapping a plurality of carbon nanotube (CNT) sheets around a core fiber; infiltrating a binding agent in between the plurality of (Continued)

CNT sheets, wherein the binding agent binds the plurality of the CNT sheets together; and removing the core fiber from the plurality of CNT sheets.

15 Claims, 8 Drawing Sheets

(51) Int. Cl.
- *B01J 23/50* (2006.01)
- *D02G 3/44* (2006.01)
- *B82Y 5/00* (2011.01)

(52) U.S. Cl.
CPC ............ *A61F 2002/0894* (2013.01); *A61F 2210/0057* (2013.01); *A61F 2210/0066* (2013.01); *B82Y 5/00* (2013.01)

(58) Field of Classification Search
CPC ........ C01B 32/162; D02G 3/448; D02G 3/36; D02G 3/44; B82Y 5/00; D10B 2101/122
See application file for complete search history.

(56) References Cited

U.S. PATENT DOCUMENTS

| | | | |
|---|---|---|---|
| 2016/0024262 A1* | 1/2016 | Lu | B29C 70/021 523/222 |
| 2018/0291535 A1* | 10/2018 | Ridley | D02G 3/326 |
| 2020/0208614 A1* | 7/2020 | Baughman | F03G 1/02 |

FOREIGN PATENT DOCUMENTS

| | | |
|---|---|---|
| WO | 2017058339 A2 | 4/2017 |
| WO | 2017165435 A2 | 9/2017 |

OTHER PUBLICATIONS

Written Opinion issued in corresponding International Application No. PCT/US2019/019233, dated Apr. 23, 2019 (6 pages).

Japanese Office Action dated Aug. 10, 2021 and issued in Japanese patent application No. 2020-544518 along with an English translation.

Notice of allowance dated Apr. 4, 2022 issued in Japanese Patent Application No. 2020-544518, along with corresponding English translation.

\* cited by examiner

HYDRAULIC MUSCLE FROM HOLLOW WRAPPED CARBON NANOTUBE YARN

CROSS REFERENCE TO RELATED APPLICATIONS

This is a national stage application of International Patent Application No. PCT/US2019/019233, filed on Feb. 22, 2019, and claims priority to U.S. Provisional Patent Application No. 62/634,122 filed on Feb. 22, 2018. The contents of these applications are hereby incorporated by reference in their entirety.

BACKGROUND

Artificial muscle devices based on elastic polymeric fibers have a wide range of applications. Artificial muscle devices that include twisted and/or coiled polymers may have the advantages of lower production cost, higher production volume, lower operation noise, and simpler design over conventional motors.

SUMMARY

In one aspect, embodiments of the invention are directed to a hydraulic muscle comprising a hollow carbon nanotube (CNT) yarn tube. The CNT yarn tube comprises: a plurality of CNT sheets twisted and wrapped in form of a hollow tube; and a binding agent infiltrated in the plurality of CNT sheets that binds the plurality of the CNT sheets together.

In one aspect, embodiments of the invention are directed to a method of manufacturing a hydraulic muscle. The method comprises: twisting and wrapping a plurality of CNT sheets around a core fiber; infiltrating a binding agent in between the plurality of CNT sheets such that the binding agent binds the plurality of the CNT sheets together; and removing the core fiber from the plurality of CNT sheets.

Other aspects and advantages of one or more embodiments disclosed herein will be apparent from the following description and the appended claims.

DETAILED DESCRIPTION

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

In general, embodiments of the invention relate to hydraulic devices that are made of hollow carbon nanotube (CNT) wrapped tubes (hereinafter, will be referred to as "CNT yarn tubes" or "hollow CNT yarn tubes") and methods of making hydraulic devices made of CNT yarn tubes. More specifically, one or more embodiments are directed to hydraulic devices that include at least one CNT yarn tube, which is made of CNT sheets/yarns (hereinafter, will be referred to as "CNT sheets") twisted and wrapped to form a hollow tube. A binding agent is infiltrated in between the CNT sheets, and works like an adhesive and binds the CNT sheets together. In one or more embodiments, the binding agent seals the CNT yarn tube and prevents a fluid inside the CNT yarn tube from leaking through the walls of the CNT yarn tube.

In one or more embodiments, when the fluid inside the CNT yarn tube applies an internal pressure on the interior walls of the CNT yarn tube, the diameter of the CNT yarn tube increases. Because the CNTs in the CNT sheets tend to maintain their length, upon increasing the diameter of the CNT yarn tube, the length of the CNT yarn tube decreases.

Figure 1:
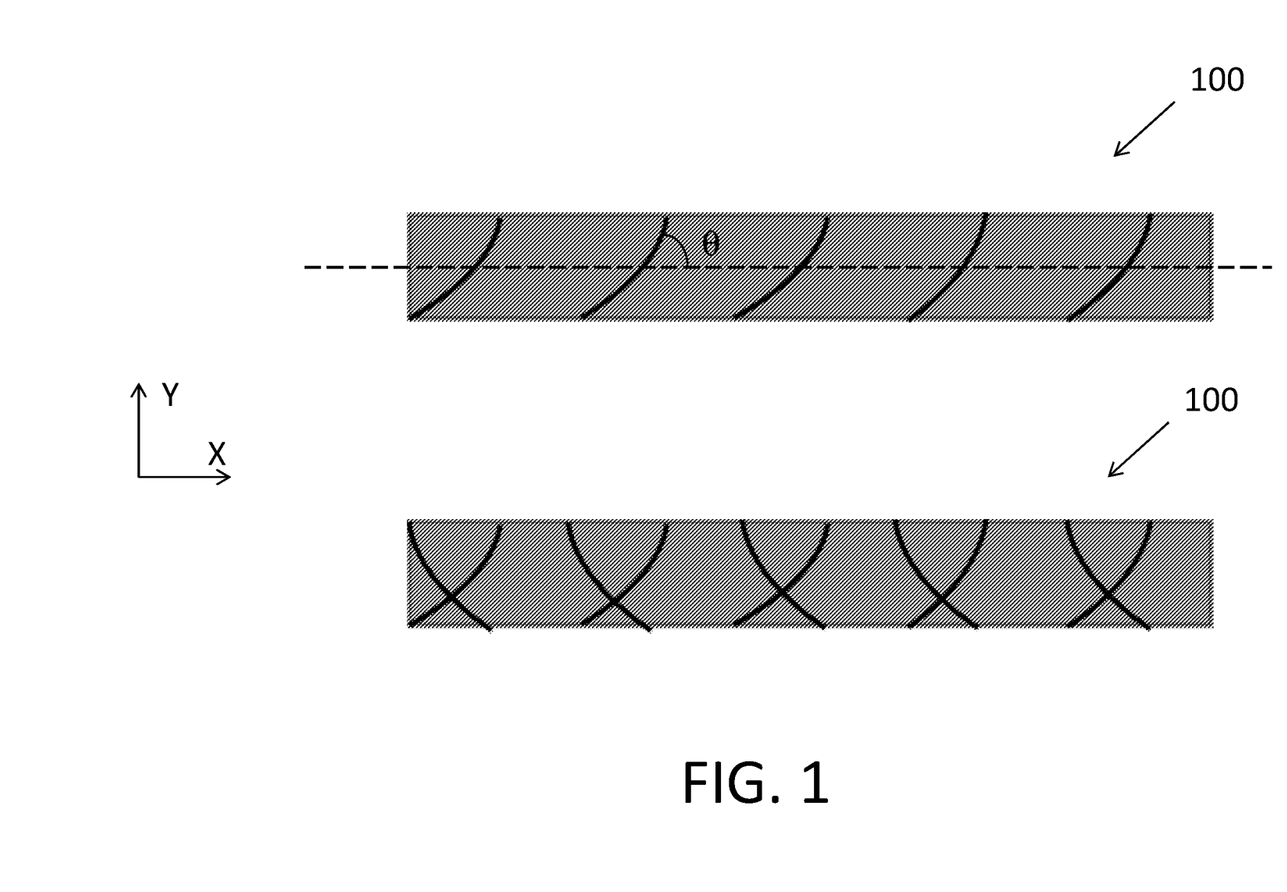
FIG. 1 shows hollow carbon nanotube (CNT) yarn tubes in accordance with one or more embodiments of the invention.

As shown in the top side of FIG. 1, the CNT sheets may be wrapped such that the CNT sheets are aligned to a bias angle (θ) less than 90 degrees with respect to a central axis of the CNT yarn tube (100). The bias angle of the CNT sheets is defined as the orientation angle of the majority of CNTs with respect to the central access of the CNT yarn tube (100). Hereinafter, a CNT yarn tube with a bias angle of less than 90 degrees is referred to as a "torsional CNT yarn tube."

In other embodiments, the CNT sheets may be braided in order to have a net bias angle of 0 degrees (i.e., to have no bias angle). For example, as shown in the bottom side of FIG. 1, the CNT sheets may be braided in opposite directions in order to maintain a zero bias angle condition for the CNT yarn tube (100).

Figure 2A:
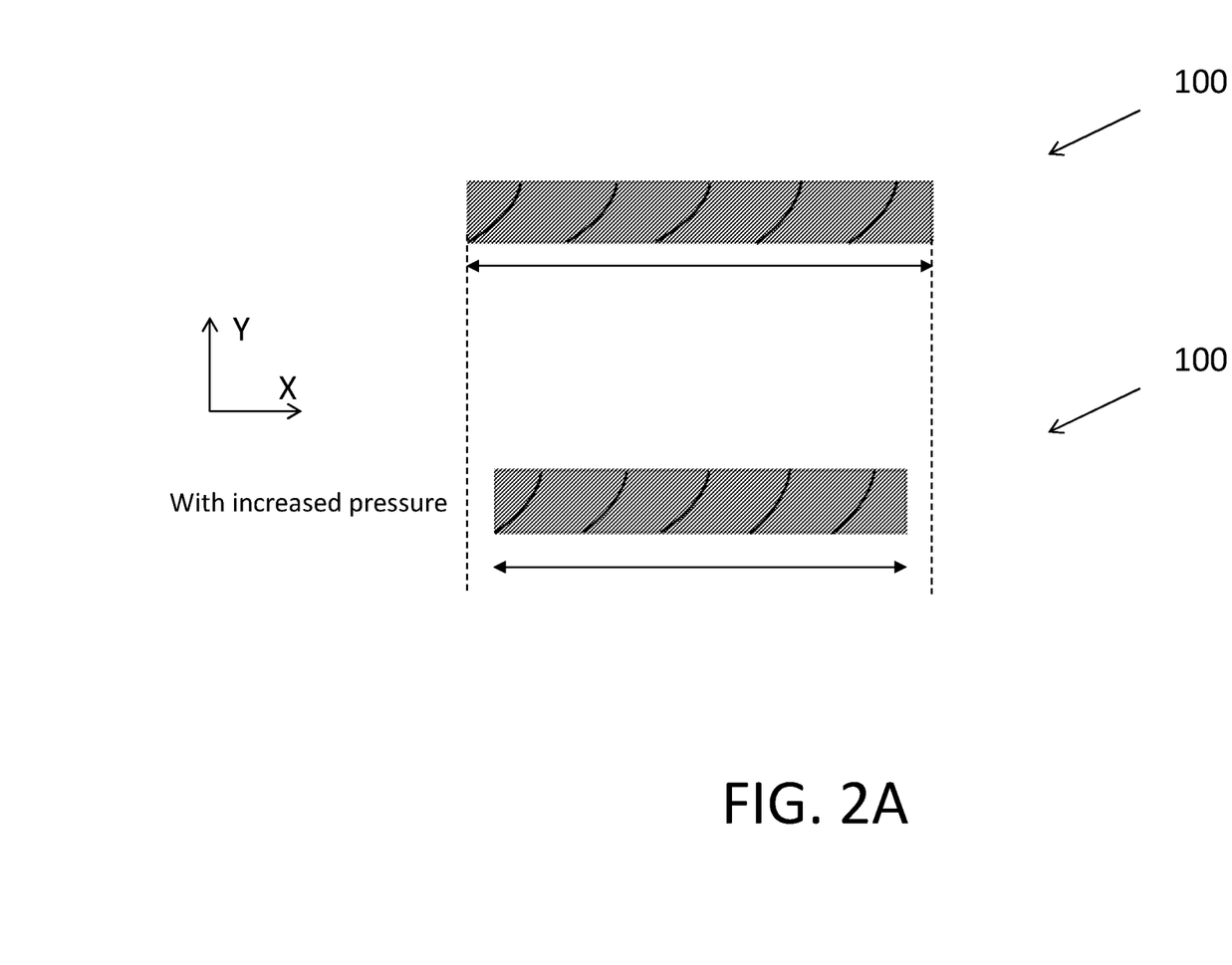
FIGS. 2A and 2B show actuations of CNT yarn tubes in accordance with one or more embodiments of the invention.
Figure 2B:
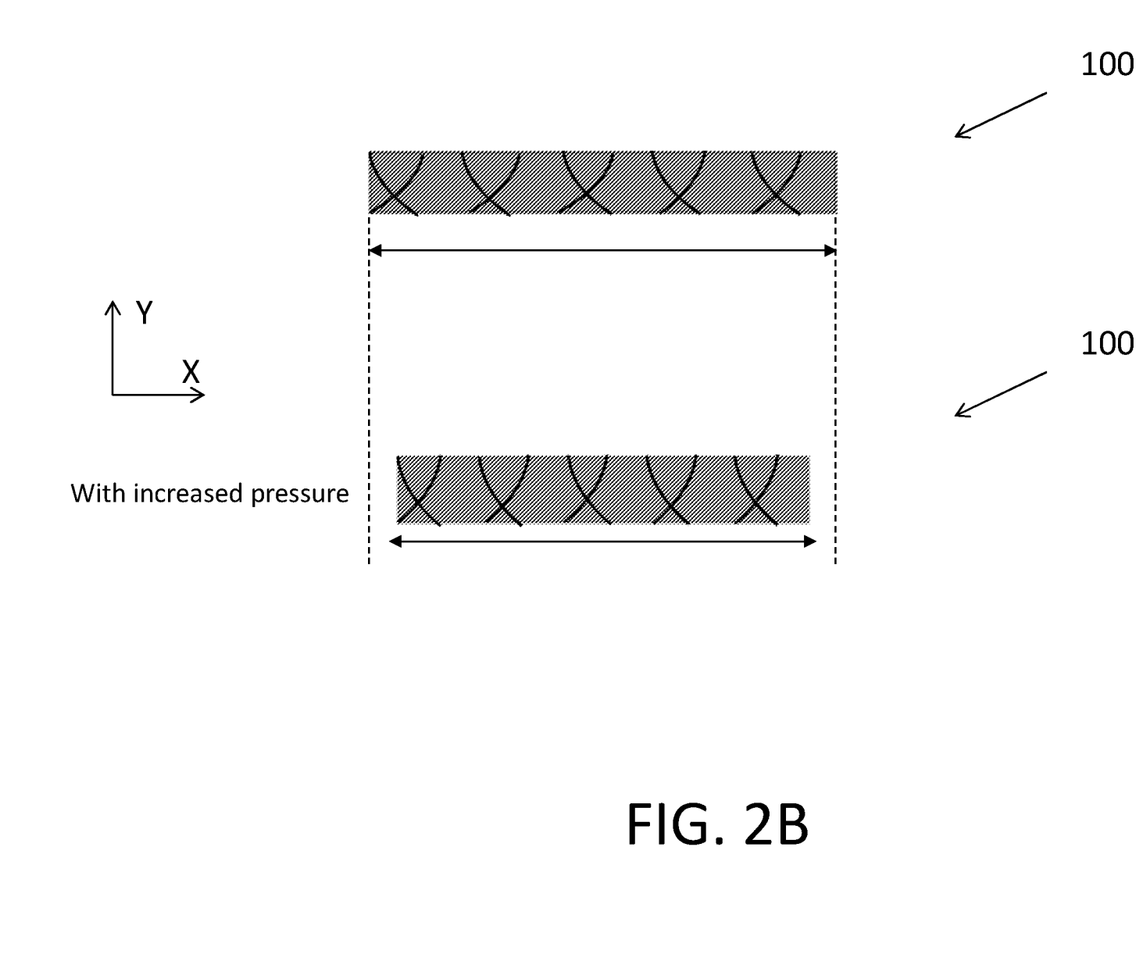

FIGS. 2A and 2B show CNT yarn tubes (200) that are actuated upon applying the internal pressure. For example, when the fluid applies an internal pressure on the interior walls of the CNT yarn tube (200), the diameter of the CNT yarn tube (200) increases. If the CNT yarn tube (200) does not rotate or the CNT yarn tube (200) is secured from rotation, an expansion in the diameter contracts the CNT yarn tube (200) along the length of the CNT yarn tube (200) (i.e., along the X axis in FIGS. 2A and B). In embodiments disclosed herein, this process is referred to as linear hydraulic actuation hereinafter. The linear hydraulic actuation of one or more embodiments may be considered similar to operations of McKibben Hydraulic/Pneumatic actuators.

In one or more embodiments, in a case where the CNT sheets in the CNT yarn tube (200) are braided in order to have no bias angle (as shown in FIG. 2B), upon linear hydraulic actuation, the CNT yarn tube (200) may not demonstrate any torsional forces because the net torque created by the pressure applied to the CNT sheets is zero. Therefore, there may be no need for securing the ends of a braided CNT yarn tube (200) from rotation in accordance with embodiments disclosed herein.

In embodiments disclosed herein, a torsional CNT yarn tube (200) (as shown in FIG. 2A) may be used for linear hydraulic actuation. In such embodiments, the ends of the torsional CNT yarn tube (200) must be secured from torsional movements.

According to one or more embodiments, although the CNT yarn tube (200) may be flexible, the CNT yarn tube (200) may be considered stiffer than conventional McKibben muscles and, therefore, embodiments disclosed herein may exert a larger force over a smaller actuation length than conventional McKibben muscles. In addition, the CNT yarn tube (200) may be advantageous over conventional McKibben muscles in applications where more stiffness is needed, for example in some flexible piping applications.

As an example, in one or more embodiments, at an internal pressure of 200 pounds per square inch (PSI), a CNT yarn tube (200) with an inner diameter of 1 millimeter (mm), may contract by up to 10% of the initial length of the CNT yarn tube (200). One of ordinary skill in the art will appreciate the relationship between the internal pressure and geometry of the CNT yarn tube (200) to the amount of length contraction in embodiments disclosed herein.

One or more embodiments disclosed herein relate to a torsional hydraulic actuator made of a torsional CNT yarn tube, where the torsional CNT yarn tube is secured from any linear movements along the central axis of the torsional CNT yarn tube, but allowed to twist freely. In such embodiments, when the fluid inside the torsional CNT yarn tube applies an internal pressure on the interior walls of the torsional CNT yarn tube, the internal pressure generates a torque. Consequently, the torsional CNT yarn tube twists freely generating a torque. In embodiments disclosed herein, this function is referred to as torsional hydraulic actuation. The torsional hydraulic actuation may be considered functionally similar to an actuation of a twisted thermal actuator, which actuates by heating and expanding a polymer in the thermal actuator.

According to one or more embodiments, the CNT yarn tube may be advantageously smaller than traditional McKibben muscles. Additionally, a torsional CNT yarn tube can advantageously actuate torsionally unlike traditional McKibben muscles, which only actuate linearly.

In one or more embodiment, the CNT sheets may be wrapped around a spring. The spring may provide sufficient stiffness to the CNT yarn tube and prevent the CNT yarn tube from collapsing and forming a kink during the hydraulic actuation (torsional or linear). If a kink forms along the CNT yarn tube, the kink may prevent fluid from flowing past the kink and, thus, prevent pressure. Accordingly, any point past the kink may not actuate with the resulting internal pressure. Therefore, a kink may reduce actuating length and strength of a CNT yarn tube.

Figure 3:
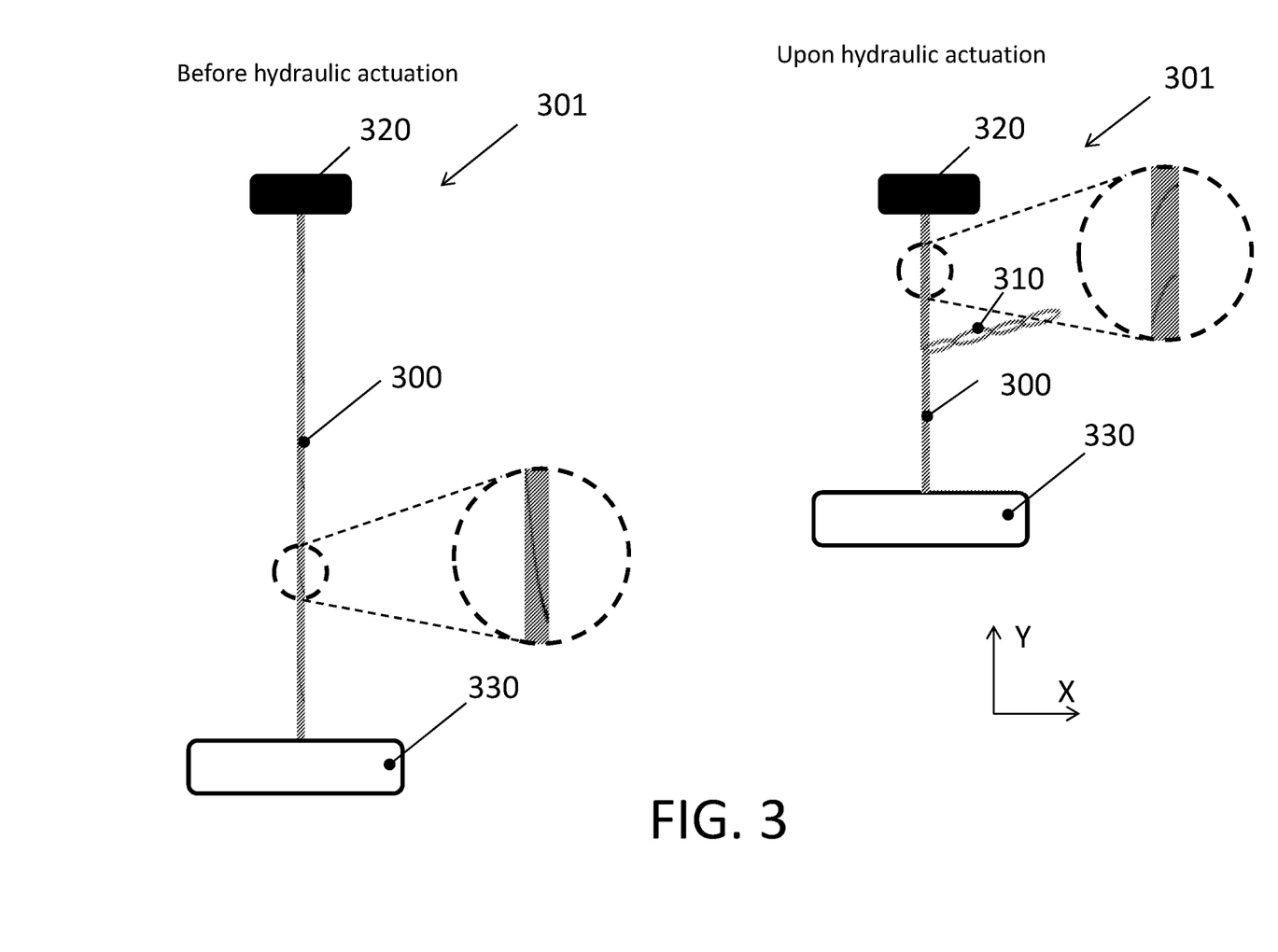
FIG. 3 shows an actuation of a snarling CNT yarn tube in accordance with one or more embodiments of the invention.

However, CNT yarn tubes according to one or more embodiment may be used in a snarling hydraulic actuator. FIG. 3 shows an example of the snarling hydraulic actuator (301) made of a torsional CNT yarn tube (300) that snarls upon actuation. In these embodiments, because the torsional CNT yarn tube (300) has a net bias angle, the ends of the torsional CNT yarn tube (300) must be secured from torsional movements. For example, a fastener (320) may be used to fasten one end of the torsional CNT yarn tube (300) and a load (330) connected to the other end of the torsional CNT yarn tube (300) may be used. An internal pressure applied on the interior walls of the torsional CNT yarn tube (300) increases the inner diameter of the torsional CNT yarn tube (300) and, thus, generates a torque. If the load (330) is small enough, the generated torque creates a snarl (310) in the torsional CNT yarn tube (300). In these embodiments, the actuated snarling hydraulic actuator (301) (shown on the right side of FIG. 3) snarls causing the torsional CNT yarn tube (300) to contract and move the load (330).

As an example, in one or more embodiments, a torsional CNT yarn tube (300) of a snarling hydraulic actuator (301) may contract by up to 28% of the initial length of the torsional CNT yarn tube (300). In other embodiments, the torsional CNT yarn tube (300) may contract by up to 90% of the initial length of the torsional CNT yarn tube (300).

In one or more embodiments, the torsional CNT yarn tube (300) may include about 10 layers of CNT sheets stacked on top of each other. In one or more embodiments, the torsional CNT yarn tube (300) may be infiltrated with Eco-Flex 0020 (manufactured by Smooth-On, INC), which functions as a binding agent. The torsional CNT yarn tube (300) may have an inner diameter of 2 mm and a length of 20 centimeters (cm).

Figure 4:
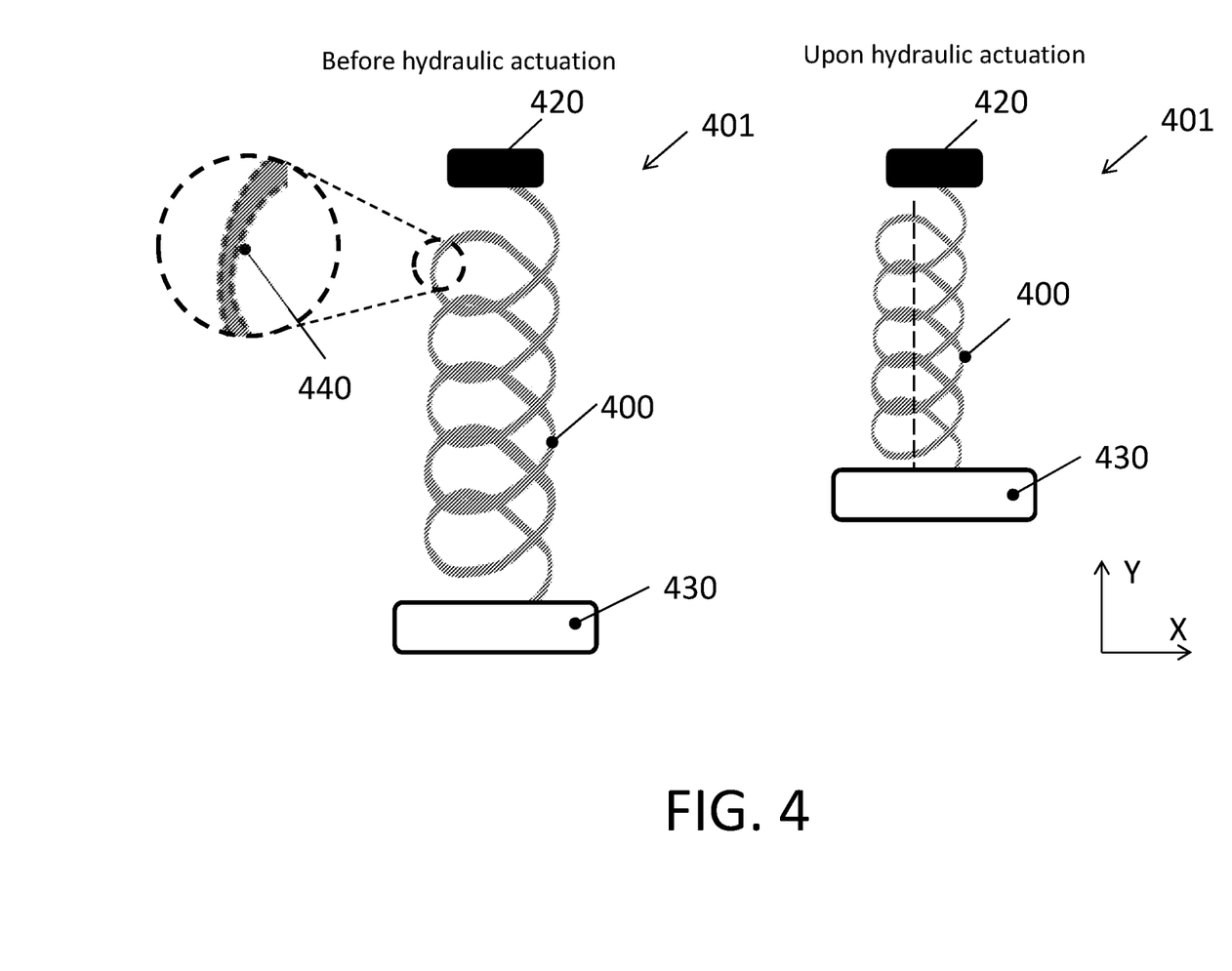
FIG. 4 shows an actuation of a coiled CNT yarn tube in accordance with one or more embodiments of the invention.

The torsional CNT yarn tube of one or more embodiments disclosed herein may be a coiled CNT yarn tube. FIG. 4 shows an example of a coiled hydraulic actuator (401) that includes the coiled CNT yarn tube (400). A fastener (420) and a load (430) may secure both ends of the coiled CNT yarn tube (400) from torsional movements. When a fluid applies an internal pressure on the interior walls of the coiled CNT yarn tube (400), the internal pressure generates a torque. Because both ends of the coiled CNT yarn tube (400) are secured from rotations, the generated torque contracts or extends the coiled CNT yarn tube (400) along the central axis of the coiled CNT yarn tube (400) (shown by the broken line parallel to the "Y" axis in FIG. 4).

In such embodiments, to maintain the coiled shape of the coiled CNT yarn tube (400), a layer of soft silicone (440) (e.g., Eco-Flex 0020) may be coated on the coiled CNT yarn tube (400). In FIG. 4, the layer of soft silicon (440) is shown by the broken lines in the magnified subset. The layer of soft silicone (440) gives enough rigidity to the coiled CNT yarn tube (400) to maintain the coiled shape, while supplying enough flexibility to the coiled CNT yarn tube (400) to move freely along the central axis of the coiled CNT yarn tube (400).

Depending on the coiling direction, the coiled CNT yarn tube may be considered homochiral or heterochiral. In homochiral coiled CNT yarn tube embodiments, the coiling direction is the same direction as the twisting direction of the CNT sheets. Upon hydraulic actuation, the length of the homochiral coiled CNT yarn tube decreases along the central axis of the homochiral coiled CNT yarn tube, as shown in FIG. 4.

In heterochiral coiled CNT yarn tube embodiments, the coiling direction is opposite to the twisting direction of the CNT sheets. Upon hydraulic actuation, the length of the heterochiral coiled CNT yarn tube increases along the central axis of the heterochiral coiled CNT yarn tube.

For example, at an internal pressure of 200 PSI, a homochiral coiled CNT yarn tube that is made of a CNT yarn tube having an inner diameter of about 1.6 mm may contract by up to 30%.

In one or more embodiments, the internal pressure may be driven thermally by heating a fluid inside the CNT yarn tube. Such fluids may be a liquid or a gas. Liquids may be generally slower to heat up and expand for actuation than gases. However, liquids may advantageously result stronger actuations. Actuating with gases may result in a faster and larger degree (or length) of actuation. In one or more embodiments, the fluid may be initially liquid and through a physical phase transition (e.g., evaporation) or a chemical phase transition (e.g., chemical reaction) create a gas to expand and actuate the CNT yarn tube.

According to one or more embodiments, no liquid plumbing or piping may be necessary to actuate the CNT yarn tubes. In other words, the ends of the CNT yarn tube may only need to be hermetically sealed to prevent the fluid from escaping the ends, and heating the fluid inside the CNT yarn tube may produce the desired internal pressure. Hereinafter, this process will be referred to as "thermal-initiated hydraulic actuation." According to these embodiments, the hermetically sealed CNT yarn tubes may be actuated without a pump. If a leak occurs, the CNT yarn tube will not actuate. Because there is no need for a pump, and the CNT yarn tube can be heated remotely, if a liquid inside the CNT yarn tube leaks, the leakage will not cause contamination or damage to equipment surrounding the leaking CNT yarn tube.

In one or more embodiments, a pump may be used to generate an internal pressure inside the CNT yarn tubes disclosed herein. An advantage of using a pump for hydraulic actuation over the thermal-initiated hydraulic actuation is that there is no need for cooling the CNT yarn tube and the fluid inside the CNT yarn tube to reverse the actuation. To reverse the actuation simply the internal pressure is released. Therefore, it may be possible to achieve a much faster actuation cycle, which is limited by the speed of a valve supplying and releasing the internal pressure.

In one or more embodiments, because CNTs may be conductive, the liquid or gas inside the CNT yarn tube may be heated by resistive heating via passing an electrical current through the CNT sheets.

In one or more embodiments, the internal pressure may be driven chemically. For example, hydrogen peroxide ($H_2O_2$) may be used as the fluid inside the CNT yarn tube. $H_2O_2$ may operate like a fuel when chemically activated, and $H_2O_2$ may quickly produce energy and internal pressure in the CNT yarn tube. Hydrazine may also be used instead of $H_2O_2$. When the volume of the CNT yarn tube is small, the amount of the chemical necessary to cause actuation is correspondingly small. For example, microliters of $H_2O_2$ may decompose into milliliters of water and oxygen; thus, significantly increasing the internal pressure of the CNT yarn tube.

In one or more embodiments, an amount of the $H_2O_2$ in the CNT yarn tube may be regulated using a valve to control an actuation rate of the CNT yarn tube. In one or more embodiments, solutions with different concentrations of water and $H_2O_2$ may be used as the fuel. To control the consecration, water and $H_2O_2$ may be fed into the CNT yarn tube via a first line (e.g., a tube or pipe) for water and a second line for $H_2O_2$. Each of the first and second lines may have a valve to regulate flow-rates of the water and $H_2O_2$. Thus, the concentration of the $H_2O_2$ in the CNT yarn tube and the actuation rate may be controlled using the regulating valve of the first line and/or the regulating valve of the second line.

According to one or more embodiments, catalysts may be used to further activate the chemical reaction of the fuel (e.g., $H_2O_2$ or Hydrazine). Such catalysts may adhere to the interior walls of the CNT yarn tube. Examples of such catalysts include silver for hydrazine and magnesium dioxide for $H_2O_2$.

In one or more embodiments, the catalyst may be disposed onto the interior walls of the CNT yarn tube by placing the CNT yarn tube into an appropriate solution of the catalyst. For example, a solution of 0.25 molar (M) potassium permanganate ($KMnO_4$) and 0.5 M sulfuric acid ($H_2SO_4$) may be used.

In accordance with embodiments disclosed herein, the temperature of the hydraulic fluid (e.g., for exothermic chemical reactions) should be less than 400 degrees Celsius to prevent damaging the CNT sheets.

FIGS. 5, 6A-6C, and 7 show preparation methods of the CNT yarn tubes in accordance with one or more embodiments disclosed herein.

Figure 5:
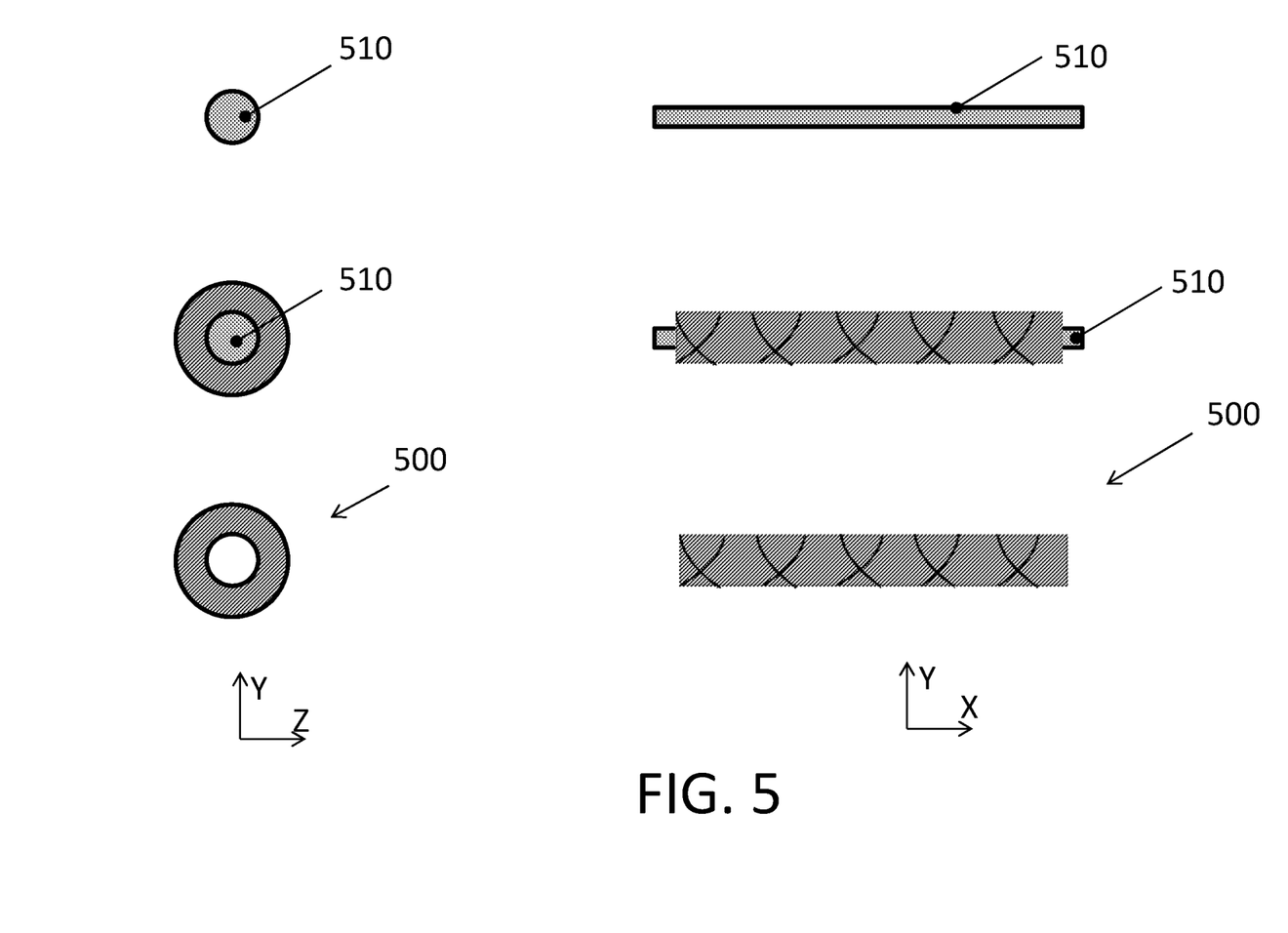
FIG. 5 shows a diagram representing a method of manufacturing a CNT yarn tube in accordance with one or more embodiments of the invention.

FIG. 5 shows side-views (on the right side of FIG. 5) and cross-sectional views (on the left side of FIG. 5) of the features in FIG. 5. As show in FIG. 5, a CNT yarn tube (500) may be manufactured by wrapping and twisting CNT sheets around a core fiber (510). The core fiber (510) is then removed from the CNT sheets to form the CNT yarn tube (500). In one or more embodiments, the core fiber (510) is a metal in order to be malleable and stiff enough to maintain its shape.

In one or more embodiments, the core fiber (510) may be a soldering wire or another metallic wire that can be removed from the wrapped CNT sheets through heating. In embodiments disclosed herein, the core finer (510) may be removed after applying a layer of soft silicone on the CNT sheets. The soft silicone layer may increase the stiffness of the CNT yarn tube (510).

Figure 6A:
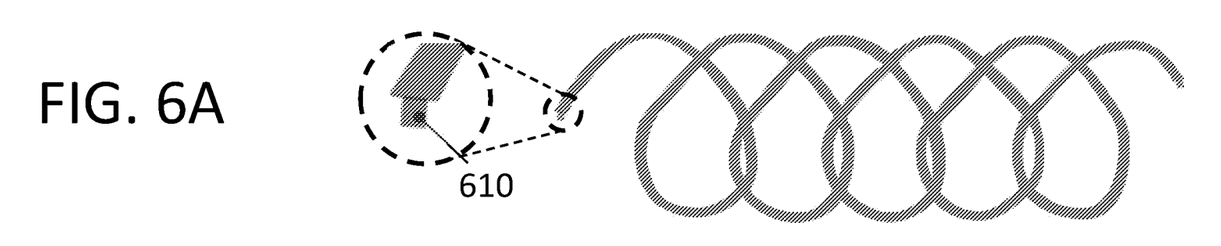
FIGS. 6A-6C show diagrams representing a method of manufacturing a coiled CNT yarn tube in accordance with one or more embodiments of the invention.
Figure 6B:
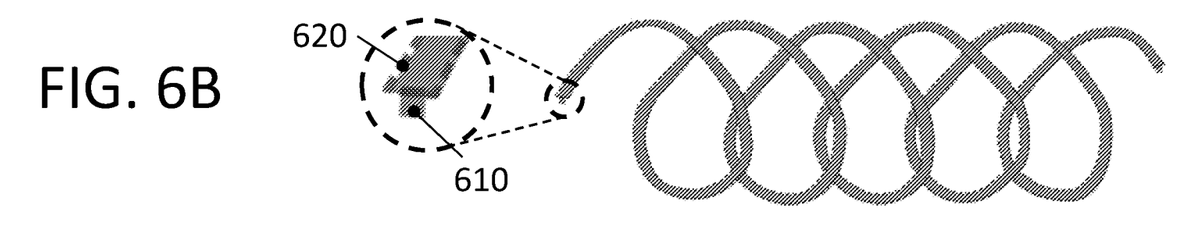
Figure 6C:
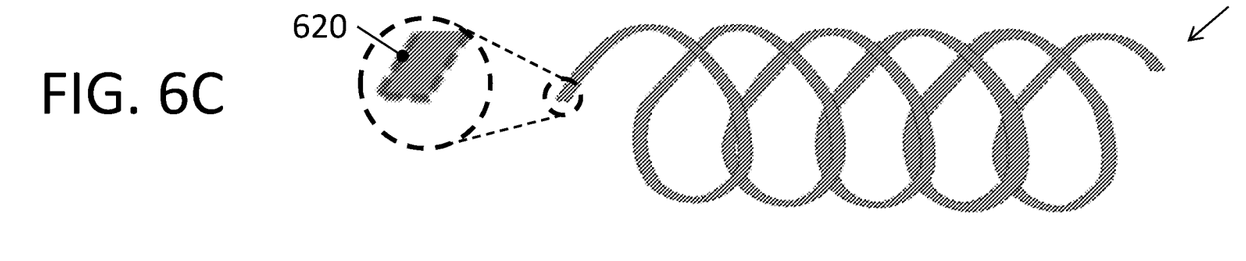

FIGS. 6A-6C show a method of preparing a coiled CNT yarn tube (600) in accordance with embodiments disclosed herein. As shown in FIG. 6A, after wrapping the CNT sheets around the core fiber (610) and infiltrating a binding agent into the CNT sheets, the core fiber (610), along with the CNT sheets and the binding agent, may be coiled. Because of the rigidity of the core fiber (610), the core fiber (610) may not lose its coiled shape. Then, as shown in FIG. 6B, while the CNT sheets are still wrapped around the core fiber (610), a layer of soft silicone (620) may be applied to the wrapped CNT sheets as a support. As shown in FIG. 6C, the core fiber (610) may then be removed. For example, the core fiber (610) may be removed by mechanically pulling the core fiber (610) out of the CNT sheets, chemical etching, melting, and draining the core fiber (610). In one or more embodiments, the core fiber (610) has a low surface energy and does not adhere to the CNT sheets; thus, the core fiber (610) can be easily removed. Other methods may be used to remove the core fiber based on the specific design and function of the coiled CNT yarn tube. Because the layer of soft silicone (620) provides enough support for the coiled CNT yarn tube (600), the coiled CNT yarn tube (600) maintains the coiled shape.

In one or more embodiments, the core fiber may be coiled before wrapping the CNT sheets around the core fiber. In such embodiments, larger diameter coils of the core fiber may make it easier to apply the CNT sheets; however, controlling the bias angle precisely in such embodiments may be considered difficult.

In one or more embodiments, the core fiber may be a spring, and the spring may be left in the coiled CNT yarn tube after wrapping the CNT sheets such that the coiled CNT yarn tube actuates with the spring inside the coiled CNT yarn tube.

In one or more embodiments, a catalyst may be deposited on the core fiber before wrapping the CNT sheets. The catalyst may adhere to the interior walls of the CNT yarn tube and when the core fiber is removed, the catalyst may remain on the interior walls of the CNT yarn tube.

Figure 7:
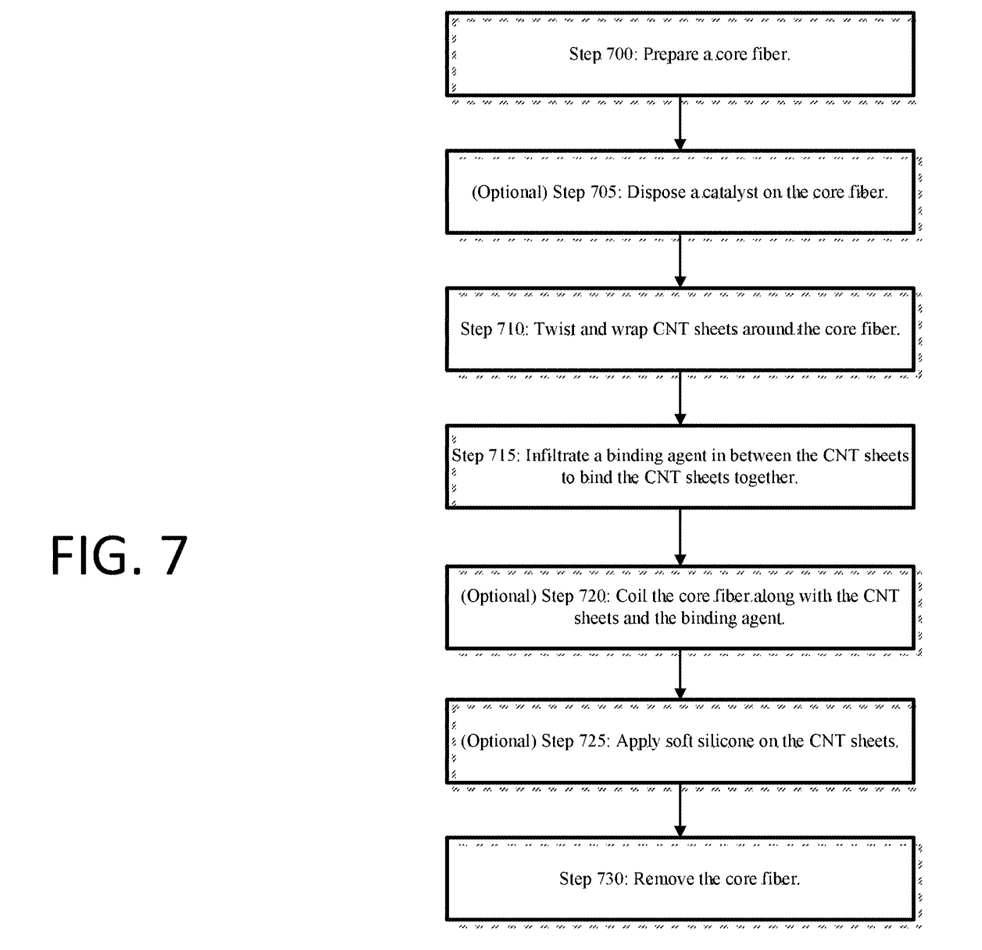
FIG. 7 shows a flowchart in accordance with one or more embodiments of the invention.

FIG. 7 shows a flowchart depicting a method for manufacturing a CNT yarn tube in accordance with embodiments herein. In one or more embodiments, one or more of the steps shown in FIG. 7 may be omitted, repeated, and/or performed in a different order than the order shown in FIG.

7. Accordingly, the scope of the invention is not limited to the specific arrangement of steps shown in FIG. 7, unless the arrangement is specified.

In Step 700, a core fiber is prepared. For example, the core fiber may be the core fiber in accordance with any of the embodiments described above.

In optional Step 705, a catalyst is disposed on the core fiber before wrapping CNT sheets on the core fiber. The catalyst may be used to initiate a chemical reaction of a chemical/fuel inside the CNT yarn tube. For example, the catalyst may be similar to the catalysts disclosed in embodiments above.

In Step 710, CNT sheets are twisted and wrapped around the core fiber. The CNT sheets may be wrapped with a specific bias angle or may be braided to have no bias angle. For example, the CNT sheets may be wrapped in accordance with embodiments disclosed above. In one or more embodiments, the catalyst adheres to interior walls of the wrapped CNT sheets.

In Step 715, a binding agent may be infiltrated in between the CNT sheets to adhere the CNT sheets together. In such embodiments, the binding agent seals the CNT yarn tube such that a hydraulic fluid inside the CNT yarn tube cannot escape from the walls of the CNT yarn tube. For example, the biding agent may be in accordance with one or more embodiments disclosed above.

In optional Step 720, to create a coiled CNT yarn tube, the core fiber along with the wrapped CNT sheets and the infiltrated binding agent are coiled. For example, coiling may be in accordance with embodiments disclosed above with respect to the coiled CNT yarn tube.

In optional Step 725, a layer of soft silicone may be applied on the wrapped CNT sheets. In such embodiments, the soft silicone layer may be applied after coiling the core fiber in Step 720. For example, the soft silicone layer may be applied in accordance with embodiments disclosed above.

In Step 730, the core fiber may be removed from the CNT sheets. In one or more embodiments, the core fiber may be removed after applying the soft silicone layer such that the soft silicone layer gives a mechanical strength to the coiled CNT sheets to maintain their coil shape without the core fiber. In some embodiments, the catalyst remains on the interior walls of the wrapped CNT sheets when the core fiber is removed.

In one or more embodiments, the core fiber may be a spring and the spring is left inside the CNT sheets (i.e., Step 730 is omitted) such that the coiled CNT yarn tube operates with the spring.

Although the disclosure has been described with respect to only a limited number of embodiments, those skilled in the art, having benefit of this disclosure will appreciate that various other embodiments may be devised without departing from the scope of the present invention. Accordingly, the scope of the invention should be limited only by the attached claims.

What is claimed is:

1. A hydraulic muscle comprising:
   a hollow carbon nanotube (CNT) actuation tube comprising:
   a plurality of CNT sheets wrapped in form of a hollow tube; and
   a binding agent infiltrated in the plurality of CNT sheets that binds the plurality of the CNT sheets together and seals the hollow CNT actuation tube from leaking, wherein
   the hollow CNT actuation tube has an inner diameter, a central axis, and a length;
   a wrapping direction of the plurality of CNT sheets and the central axis forms a bias angle at a first value larger than 0 degree and smaller than 90 degrees; and
   an increase of an internal pressure of the hollow CNT actuation tube causes an increase in the inner diameter, a decrease in the length, and a change of the bias angle from the first value to a second value.

2. The hydraulic muscle according to claim 1, further comprising a spring, wherein
   the plurality of CNT sheets are wrapped around outside surfaces of the spring.

3. The hydraulic muscle according to claim 1, wherein
   two opposite ends of the hollow CNT actuation tube are prevented from rotating so that
   when the internal pressure inside the hollow CNT actuation tube is applied, the hollow CNT actuation tube creates a torque inside the hollow CNT actuation tube such that the hydraulic muscle snarls along the length of the hollow CNT actuation tube.

4. The hydraulic muscle according to claim 1, wherein
   the hollow CNT actuation tube has a shape of a coil,
   two opposite ends of the hollow CNT actuation tube are prevented from rotating,
   the hydraulic muscle further comprises a supporting material disposed on the hydraulic muscle, preventing the hydraulic muscle from uncoiling, and
   when the internal pressure inside the hollow CNT actuation tube is applied, the hollow CNT actuation tube creates a torque inside the hollow CNT actuation tube that changes a length of the hydraulic muscle linearly along a central axis of the coil of the hydraulic muscle.

5. The hydraulic muscle according to claim 4, further comprising a spring, wherein the plurality of CNT sheets are wrapped around the spring.

6. The hydraulic muscle according to claim 4, wherein the supporting material is a silicone layer.

7. The hydraulic muscle according to claim 4, wherein
   the hydraulic muscle is homochiral, and
   the torque inside the hollow CNT actuation tube contracts the hydraulic muscle linearly along the central axis of the coil of the hydraulic muscle.

8. The hydraulic muscle according to claim 4, wherein
   the hydraulic muscle is heterochiral, and
   when the torque inside the hollow CNT actuation tube extends the hydraulic muscle linearly along the central axis of the coil of the hydraulic muscle.

9. The hydraulic muscle according to claim 1, wherein
   two opposite ends of the hollow CNT actuation tube are prevented from linear actuation, and
   when the internal pressure inside the hollow CNT actuation tube is applied, the hollow CNT actuation tube creates a torque inside the hollow CNT actuation tube that twists the CNT yarn tube along a direction of twisting the plurality of CNT sheets.

10. The hydraulic muscle according to claim 1, wherein
    a gas or liquid inside the hollow CNT actuation tube is heated via an electrical current passing the plurality of CNT sheets, and
    a thermal expansion of the gas or liquid actuates the hollow CNT actuation tube.

11. A method of manufacturing a hydraulic muscle, the method comprising:

wrapping a plurality of carbon nanotube (CNT) sheets around a core fiber with a bias angle at a first value greater than 0 degree and smaller than 90 degrees in form of a hollow CNT tube;

infiltrating a binding agent in between the plurality of CNT sheets, wherein
the binding agent binds the plurality of the CNT sheets together and seals the plurality of CNT sheets from leaking; and removing the core fiber from the plurality of CNT sheets, wherein
an increase of an internal pressure of the hollow CNT tube causes an increase in a diameter of the hollow CNT tube, a decrease in a length of the hollow CNT tube, and a change of the bias angle of the hollow CNT tube from the first value to a second value.

12. The method according to claim 11, further comprising:
coiling the core fiber along with the plurality of CNT sheets and the binding agent; and
applying a silicone layer on the plurality of CNT sheets as a support before removing the core fiber.

13. The method according to claim 11, further comprising:
disposing a catalyst on the core fiber before wrapping the plurality of CNT sheets around the core fiber, wherein
the catalyst adheres to interior walls of the wrapped plurality of CNT sheets;
the catalyst stays on the interior walls of the wrapped plurality of CNT sheets when the core fiber is removed, and
the catalyst initiates a chemical reaction of a chemical/fuel inside the CNT yarn tube.

14. The method according to claim 13, wherein the chemical/fuel is a hydrazine and the catalyst is silver.

15. The method according to claim 13, wherein the chemical/fuel is hydrogen peroxide ($H_2O_2$) and the catalyst is magnesium dioxide.

* * * * *